(12) United States Patent
Mazur et al.

(10) Patent No.: US 10,980,287 B2
(45) Date of Patent: *Apr. 20, 2021

(54) AEROSOL-GENERATING SYSTEM AND METHOD OF DISPENSING LIQUID AEROSOL-FORMING SUBSTRATE WITH PUMPED AIR

(71) Applicant: Mycronic AB, Taby (SE)

(72) Inventors: Ben Mazur, Bristol (GB); Eva Saade Latorre, Neuchatel (CH); Alain Tabasso, Essertines-sur-Yverdon (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/875,355

(22) Filed: May 15, 2020

(65) Prior Publication Data

US 2020/0305315 A1    Sep. 24, 2020

Related U.S. Application Data

(63) Continuation of application No. 15/825,584, filed on Nov. 29, 2017, now Pat. No. 10,653,185, which is a
(Continued)

(30) Foreign Application Priority Data

Nov. 29, 2016  (EP) ..................... 16201201

(51) Int. Cl.
*A24F 47/00*    (2020.01)
*F04B 19/00*   (2006.01)
(Continued)

(52) U.S. Cl.
CPC ............ *A24F 47/008* (2013.01); *A24F 40/48* (2020.01); *A61M 11/02* (2013.01);
(Continued)

(58) Field of Classification Search
CPC ..................................... A24F 47/008
See application file for complete search history.

(56) References Cited

U.S. PATENT DOCUMENTS 5,700,245 A   12/1997  Sancoff et al.
6,234,167 B1   5/2001  Cox et al.
(Continued)

FOREIGN PATENT DOCUMENTS

CN    202015398 U   10/2011
DE      1814775 U    7/1960
(Continued)

OTHER PUBLICATIONS

European Search Report for European Application No. 16201201 dated May 17, 2017.
(Continued)

*Primary Examiner* — James Harvey
(74) *Attorney, Agent, or Firm* — Harness, Dickey & Pierce, P.L.C.

(57) ABSTRACT

An aerosol-generating system may include a liquid storage portion, a vaporizer, and a pump. The liquid storage portion may be configured to store a liquid aerosol-forming substrate. The vaporizer may be configured to volatilize the liquid aerosol-forming substrate. The pump may be configured to pump air into the liquid storage portion so as to push out a volume of the liquid aerosol-forming substrate from the liquid storage portion and to supply the volume of the liquid aerosol-forming substrate to the vaporizer. A method for generating an aerosol may be performed with the system.

15 Claims, 2 Drawing Sheets

Related U.S. Application Data continuation of application No. PCT/EP2017/077676, filed on Oct. 27, 2017.

(51) Int. Cl.

| | |
|---|---|
| *A61M 15/06* | (2006.01) |
| *A61M 11/02* | (2006.01) |
| *F04F 5/24* | (2006.01) |
| *A61M 15/00* | (2006.01) |
| *F04B 45/047* | (2006.01) |
| *F04B 43/04* | (2006.01) |
| *A61M 11/04* | (2006.01) |
| *A24F 40/48* | (2020.01) |
| *H05K 13/08* | (2006.01) |
| *B65G 1/137* | (2006.01) |
| *H05K 5/00* | (2006.01) |
| *H05K 13/00* | (2006.01) |
| *H05K 13/02* | (2006.01) |
| *A61M 16/00* | (2006.01) |
| *H05K 13/04* | (2006.01) |
| *G06K 7/10* | (2006.01) |
| *G06K 7/14* | (2006.01) |

(52) U.S. Cl.
CPC ...... *A61M 11/042* (2014.02); *A61M 15/0028* (2013.01); *A61M 15/0036* (2014.02); *A61M 15/06* (2013.01); *B65G 1/1375* (2013.01); *F04B 19/006* (2013.01); *F04B 43/043* (2013.01); *F04B 45/047* (2013.01); *F04F 5/24* (2013.01); *H05K 5/0017* (2013.01); *H05K 13/0084* (2013.01); *H05K 13/021* (2013.01); *H05K 13/086* (2018.08); *A61M 15/0015* (2014.02); *A61M 2016/0024* (2013.01); *A61M 2205/07* (2013.01); *A61M 2205/50* (2013.01); *A61M 2205/8206* (2013.01); *G06K 7/10297* (2013.01); *G06K 7/1413* (2013.01); *H05K 13/0419* (2018.08)

(56) References Cited

U.S. PATENT DOCUMENTS

| | | | |
|---|---|---|---|
| 8,881,737 | B2 | 11/2014 | Collett et al. |
| 9,420,829 | B2 | 8/2016 | Thorens et al. |
| 2014/0283855 | A1 | 9/2014 | Hawes et al. |
| 2015/0122277 | A1 | 5/2015 | Frobisher et al. |
| 2016/0021931 | A1 | 1/2016 | Hawes et al. |
| 2017/0172210 | A1* | 6/2017 | Bright .................. H05B 1/0244 |
| 2017/0172212 | A1 | 6/2017 | Phillips et al. |
| 2017/0280776 | A1* | 10/2017 | Manca .................... H05B 3/04 |
| 2018/0146709 | A1 | 5/2018 | Bessant et al. |
| 2018/0146710 | A1 | 5/2018 | Bessant et al. |
| 2018/0146711 | A1 | 5/2018 | Mazur et al. |
| 2018/0168229 | A1 | 6/2018 | Mazur |
| 2019/0320717 | A1 | 10/2019 | Tabasso et al. |
| 2019/0364965 | A1* | 12/2019 | Xiao ..................... A61M 11/007 |
| 2020/0038601 | A1* | 2/2020 | Hepworth ............. A61M 15/06 |
| 2020/0078541 | A1* | 3/2020 | Lewis .................. A61M 11/042 |
| 2020/0196678 | A1* | 6/2020 | Chen ...................... A24F 40/57 |

FOREIGN PATENT DOCUMENTS

| | | |
|---|---|---|
| EA | 23124 B1 | 4/2016 |
| RU | 2603739 C2 | 11/2016 |
| WO | WO-2013/083638 A1 | 6/2013 |
| WO | WO-2014/153515 A1 | 9/2014 |

OTHER PUBLICATIONS

Written Opinion for Application No. PCT/EP2017/077676 dated Jan. 17, 2018.

Russian Decision to Grant including the Search Report dated Nov. 27, 2019 for corresponding Russian Application No. 2019120228/12(039276).

\* cited by examiner

AEROSOL-GENERATING SYSTEM AND METHOD OF DISPENSING LIQUID AEROSOL-FORMING SUBSTRATE WITH PUMPED AIR

CROSS-REFERENCE TO RELATED APPLICATIONS

This is a continuation of U.S. application Ser. No. 15/825,584, filed Nov. 29, 2017, which is a continuation of and claims priority to PCT/EP2017/077676, filed on Oct. 27, 2017, and further claims priority to EP 16201201.7, filed on Nov. 29, 2016, the disclosures of each of which are incorporated herein by reference in their entirety.

BACKGROUND

Field

Example embodiments relate to aerosol-generating systems (which may also be referred to as electronic vaping systems), including handheld electrically operated aerosol-generating systems in which the aerosol-forming substrate is liquid and contained in a liquid storage portion.

Description of Related Art

Aerosol-generating systems may comprise an aerosol-generating device and an aerosol-generating article incorporating a liquid storage portion for storing a liquid aerosol-forming substrate. The aerosol-generating device may comprise a pump and a vaporizer. During the operation of such an aerosol-generating system, the pump receives the liquid aerosol-forming substrate from the liquid storage portion and pumps the received liquid aerosol-forming substrate to the vaporizer. The vaporizer applies heat to the liquid aerosol-forming substrate by a heater. By heating the liquid aerosol-forming substrate, an aerosol is generated.

The orientation of the aerosol-generating system may vary during its operation. Depending on the orientation, air bubbles may be sucked through the pump. In such a case, undesired bursts of liquid aerosol-forming substrate may be delivered to the vaporizer. Thus, the volume of aerosol generated by the vaporizer may vary per pump activation and may differ from a desired quantity. Moreover, over the long term, the pump may be damaged by the pumped air bubbles due to cavity pitting, its performance may deteriorate, and its lifetime may be reduced. A liquid aerosol-forming substrate may be relatively viscous. However, the pumps commercially available for use in aerosol-generating systems may have been designed for other purposes (e.g., for pumping water-based solutions which are in a range of 10 to 500 times more fluid and less viscous than liquid aerosol-forming substrates for aerosol-generating systems). Thus, pumping a relatively viscous liquid aerosol-forming substrate and supplying a volume of such a liquid may present challenges for such a pump. Moreover, the lifetime of the pump may be adversely affected from pumping a relatively viscous liquid aerosol-forming substrate instead of a water-based solution.

SUMMARY

An aerosol-generating system may comprise a liquid storage portion, a vaporizer, and a pump. The liquid storage portion is configured to store a liquid aerosol-forming substrate. The vaporizer is configured to volatilize the liquid aerosol-forming substrate. The pump may be configured to pump an incoming volume of air into the liquid storage portion so as to displace an outgoing volume of the liquid aerosol-forming substrate from the liquid storage portion and to supply the outgoing volume of the liquid aerosol-forming substrate to the vaporizer.

The pump may be arranged upstream from the liquid storage portion.

The pump may be a micro-pump configured to pump the incoming volume of the air and to displace the outgoing volume of the liquid aerosol-forming substrate per pump activation.

The pump may be configured such that only air enters the pump during the pump activation.

The vaporizer may include a heater configured to heat the outgoing volume of the liquid aerosol-forming substrate.

The aerosol-generating system may further comprise a main body defining a chamber into which the outgoing volume of the liquid aerosol-forming substrate is supplied. The heater may be arranged inside the chamber downstream from an outlet of the liquid storage portion.

The aerosol-generating system may further comprise an outlet tube in fluidic communication with the liquid storage portion. The outlet tube may have an open end configured to direct the supply of the outgoing volume of the liquid aerosol-forming substrate from the liquid storage portion to the vaporizer.

The liquid storage portion may include a collecting section and an inhibiting section. The collecting section may be configured to collect the incoming volume of the air from the pump. The inhibiting section may be configured to inhibit the incoming volume of the air from passing to the vaporizer.

The collecting section and the inhibiting section may be in a form of a separating unit configured to separate the liquid storage portion into a first storage volume and a second storage volume. The first storage volume may be coupled to the pump. The second storage volume may be coupled to the vaporizer. The separating unit may be configured to permit a passage of the liquid aerosol-forming substrate and to inhibit a passage of the incoming volume of the air from the first storage volume to the second storage volume.

The liquid storage portion may be configured to be coupled to at least one of the pump and the vaporizer by a coupling so as to be hermetically sealed.

A method for generating an aerosol may comprise storing a liquid aerosol-forming substrate in a liquid storage portion of an aerosol-generating system. The method may additionally comprise pumping an incoming volume of air into the liquid storage portion to displace an outgoing volume of the liquid aerosol-forming substrate from the liquid storage portion to a vaporizer of the aerosol-generating system. The method may further comprise volatilizing the outgoing volume of the liquid aerosol-forming substrate with the vaporizer.

The pumping of the incoming volume of the air to displace the outgoing volume of the liquid aerosol-forming substrate may be performed per pump activation with a micro-pump.

The pumping may be performed such that the outgoing volume of the liquid aerosol-forming substrate is free of air bubbles.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

One or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to some example embodiments, there is provided an aerosol-generating system (which may also be referred to as an electronic vaping system) comprising a liquid storage portion for storing a liquid aerosol-forming substrate, a pump, and a vaporizer. The vaporizer is configured for volatilizing liquid aerosol-forming substrate. The pump is configured for pumping air into the liquid storage portion to push out a volume of the liquid aerosol-forming substrate from the liquid storage portion, and to supply the pushed out volume of aerosol-forming substrate to the vaporizer.

The pump is configured to push or compress air into the liquid storage portion storing the liquid aerosol-forming substrate. The air pushed or compressed into the liquid storage portion displaces the liquid aerosol-forming substrate such that a volume of the liquid aerosol-forming substrate is dispensed (e.g., air-bubble free) from the liquid storage portion to the vaporizer. The volume of liquid aerosol-forming substrate dispensed to the vaporizer depends on the volume of compressed air pumped into the liquid storage portion. In an example embodiment, the pump is arranged upstream of the liquid storage portion and is not interposed between the liquid storage portion and the vaporizer. Thus, the liquid aerosol-forming substrate is not pumped through the pump in such an instance. Therefore, the problems related to pumping a liquid aerosol-forming substrate having a relatively high viscosity through a pump may be mitigated or avoided. As the pump only pumps air in the above example, the pump will not be damaged by the cavity pitting of air bubbles that may be incorporated in a pumped liquid depending on the orientation of the aerosol-generating system. Therefore, the aerosol-generating system is capable of reliably delivering an intended volume of liquid aerosol-forming substrate to the vaporizer and volatilizing the delivered volume of liquid aerosol-forming substrate in a wide range of orientations of the aerosol-generating system (e.g., independent of the orientation of the aerosol-generating system illustrated in the drawings).

The pump may be arranged upstream of the liquid storage portion. As used herein, the terms "upstream", "downstream", "proximal", "distal", "front" and "rear", are used to describe the relative positions of components, or portions of components, of the aerosol-generating system in relation to the direction in which a vapor or aerosol flows through the aerosol-generating system. The aerosol-generating system may comprise a mouth end through which an aerosol exits the aerosol-generating system. The mouth end may also be referred to as the proximal end. A negative pressure may be applied to the proximal or mouth end of the aerosol-generating system in order to draw an aerosol from the aerosol-generating system. The aerosol-generating system comprises a distal end opposite to the proximal or mouth end. The proximal or mouth end of the aerosol-generating system may also be referred to as the downstream end. The distal end of the aerosol-generating system may also be referred to as the upstream end. As the pump is arranged upstream of the liquid storage portion, the pump is arranged closer to the distal end compared to the liquid storage portion. Components, or portions of components, of the aerosol-generating system may be described as being upstream or downstream of one another based on their relative positions between the proximal, downstream or mouth end and the distal or upstream end of the aerosol-generating system.

The aerosol-generating system may be configured for vaporizing liquid aerosol-forming substrates having a relatively high viscosity as compared to water. The viscosity of such a liquid aerosol-forming substrate may be in the range from about 10 to 500 Millipascal-seconds (e.g., in the range from about 17 to 86 Millipascal-seconds (mPa·s)).

The pump may be configured such that only air enters the pump during pump activation. Thus, in an example embodiment, no viscous liquid aerosol-forming substrate passes through the pump.

The pump may be a micropump configured to pump a desired or predetermined volume of air per pump activation.

The pump may be configured to push out a desired or predetermined volume of the liquid aerosol-forming substrate from the liquid storage portion to the vaporizer per pump activation. The liquid aerosol-forming substrate is essentially incompressible such that the volume of the liquid aerosol-forming substrate does not depend upon the pressure of the liquid aerosol-forming substrate.

The pump can be tuned for pushing a desired volume of liquid aerosol-forming substrate to the vaporizer. For pushing out a desired volume of liquid aerosol-forming substrate from the liquid storage portion, a certain volume of air must be pumped into the liquid storage portion by the pump. The compressed air pumped into the liquid storage portion occupies the volume of the liquid being pushed out from the liquid storage portion by the compressed air. To keep the compressed air at a certain pressure within the liquid storage portion, a one-way valve may be provided at the inlet of the liquid storage portion. In an example embodiment, the pump pumps air of constant pressure into the liquid storage portion such that the volume of pumped air corresponds to the volume of liquid aerosol-forming substrate being pushed out. The pump may allow an on-demand delivery of liquid-aerosol-forming substrate at a relatively low flow rate of, for example, approximately 0.5 to 2 microliters per second for intervals of variable or constant duration. The flow rate of the liquid aerosol-forming substrate delivered to the vaporizer may depend on a pumping frequency of the pump. For achieving a desired flow rate of the liquid aerosol-forming substrate, a suitable pumping frequency of the pump may be determined from a lookup table storing a correspondence between specific desirable flow rates and specific operable pumping frequencies. A desired flow rate of the liquid aerosol-forming substrate may be achieved by appropriately setting or adjusting the pumping frequency based on the lookup table.

In an example embodiment, the aerosol-generating system comprises a tube through which the volume of the liquid aerosol-forming substrate is supplied from the liquid storage portion to the vaporizer arranged downstream of an open end of the tube.

The tube may be a nozzle. The tube may comprise any appropriate material, for example, glass, silicone, metal (e.g., stainless steel), or plastics material (e.g., polyether ether ketone (PEEK)). The size of the tube may match that of the outlet of the liquid storage portion. For example, the tube may have a diameter of about 1 to 2 millimetres, but other sizes are possible. The tube may be a capillary nozzle having a diameter of about 1 millimeter, for example, a glass nozzle, connected to the outlet of the liquid storage portion via silicone tubing. The tube may comprise a capillary tube. The cross-section of the capillary tube may be circular, ellipsoidal, triangular, rectangular, or any other suitable shape for conveying liquid. At least a width dimension of the cross-sectional area of the capillary tube may be sufficiently small such that capillary forces are present. At the same time, the cross-sectional area of the capillary tube may be sufficiently large such that a suitable volume of liquid aerosol-forming substrate can be conveyed to the heating element. The cross-sectional area of the capillary tube may be below 4 square millimetres (e.g., below 1 square millimetre, or below 0.5 square millimetres).

In an example embodiment, the vaporizer comprises a heater for heating the supplied volume of liquid aerosol-forming substrate. The heater may be any device suitable for heating the liquid aerosol-forming substrate and volatilizing at least a part of the liquid aerosol-forming substrate in order to form an aerosol. The heater may be a heated coil, a heated capillary, a heated mesh, or a heated metal plate. The heater may be a resistive heater which receives electrical power and transforms at least part of the received electrical power into heat energy. The heater may comprise only a single heating element or a plurality of heating elements. The temperature of the heating element or elements may be controlled by electronic circuitry.

The vaporizer may comprise, as a heating element, a heating coil extending from the tube in longitudinal direction. The heating coil may be mounted transverse to the tube. The heating coil may overlap with the open end of the tube for up to 3 millimetres (e.g., for up to 1 millimetre). In some examples, there may be a distance between the open end of the tube and the heating coil. The length of the heating coil may be 2 millimetres to 9 millimetres (e.g., 3 millimetres to 6 millimetres). The diameter of the heating coil may be chosen such that one end of the heating coil can be mounted around the tube. The diameter of the heating coil may be 1 millimetre to 5 millimetres (e.g., 2 millimetres to 4 millimetres).

The vaporizer may comprise, as a heating element, a conical heater extending from the tube in longitudinal direction. The conical heater may overlap with the open end of the tube. In some examples, there may be a distance of 0.1 millimetres to 2 millimetres between the open end of the tube and the conical heater (e.g., 0.1 millimetres to 1 millimetre). The slant height of the conical heater may be 2 millimetres to 7 millimetres (e.g., 2.5 millimetres to 5 millimetres). The diameter of the conical heater in a cross-sectional view may increase, when following the slant height from one end to the other, from a first diameter to a second diameter. The first diameter may be 0.1 millimetres to 2 millimetres (e.g., 0.1 millimetres to 1 millimetre). The second diameter may be 1.2 millimetres to 3 millimetres (e.g., 1.5 millimetres to 2 millimetres). In a non-limiting embodiment, the conical heater is arranged such that the liquid aerosol-forming substrate exiting from the tube passes the conical heater at the first diameter before the second diameter. The first diameter of the conical heater may be chosen such that one end of the conical heater can be mounted around the tube.

The vaporizer may comprise, as a heating element, a flat heater with, for example, a solid or mesh surface. Alternatively, the vaporizer may comprise, as a heating element, a mesh heater. In another instance, the vaporizer may comprise, as a heating element, an arrangement of filaments.

The vaporizer may comprise at least one of a solid, flexible, porous, and perforated substrate onto which the heating element may be, for example, at least one of mounted, printed, deposited, etched, and laminated. The substrate may be a polymeric or ceramic substrate.

Both the pump and the heater may be triggered by a puff detection system. Alternatively, the pump and the heater may be triggered by pressing an on-off button, which may be held for a desired duration.

The aerosol-generating system may comprise a chamber into which the volume of the liquid aerosol-forming substrate is supplied. The heater of the vaporizer may be arranged inside the chamber downstream of an outlet of the liquid storage portion.

The liquid storage portion may be configured for storing the liquid aerosol-forming substrate to be supplied to the vaporizer and for receiving air from the pump. The liquid storage portion may be configured as a container or a reservoir for storing the liquid aerosol-forming substrate.

The liquid storage portion may comprise means for collecting the air received from the pump and means for inhibiting the air pumped into the liquid storage portion for passage to the vaporizer. In order to prevent a reverse flow of the received air back to the pump, the liquid storage portion may comprise a one-way valve as an inlet for receiving air from the pump.

The means for collecting the air received from the pump and the means for inhibiting the air pumped into the liquid storage portion for passage to the vaporizer may be a separating unit which separates the liquid storage portion into a first storage volume and second storage volume. The first storage volume is coupled to the pump for receiving air. The second storage volume is coupled to the vaporizer. The separating unit is configured to allow the liquid aerosol-forming substrate to pass and to inhibit passage of the air from the first to the second storage volume. The separating unit may be implemented by providing within the liquid storage portion at least one dividing wall between the first and the second storage volume and at least one gap or valve (e.g., a one-way valve) for passing liquid aerosol-forming substrate essentially without air bubbles from the first to the second storage volume. The separating unit may be configured such that the gap or the valve is located below the fill level of the liquid aerosol-forming substrate in the first storage volume over a wide range of orientations of the liquid storage portion. In this way, the separating unit enables air bubble free liquid dispensing over a wide range of orientations of the liquid storage portion.

The liquid storage portion may be configured to be coupled to at least one of the pump and the vaporizer by a respective coupling so as to be hermetically sealed from the surrounding atmosphere. The couplings may be configured as self-healing pierceable membranes. The membranes may hinder or avoid undesired leaking of the liquid aerosol-forming substrate stored in the liquid storage portion. The liquid storage portion may be configured as a replaceable tank or container. For coupling the replaceable liquid storage portion to the pump and/or the vaporizer, a respective needle-like hollow tube may be pierced through a respective membrane. When the pump and/or the vaporizer are coupled to the liquid storage portion, the membranes may hinder or avoid the undesired leaking of the liquid aerosol-forming substrate and the leaking of air from and into the liquid storage portion.

The aerosol-generating system may comprise a main unit and a cartridge. The cartridge may be removably coupled to the main unit. The main unit may comprise a power supply. The liquid storage portion may be provided in the cartridge, and the pump may be provided in the main unit. The main unit may further comprise the vaporizer.

The aerosol-generating system may further comprise electronic circuitry connected to the vaporizer and to an electrical power source. The electronic circuitry may be configured to monitor the electrical resistance of the vaporizer. The electronic circuitry may also be configured to control the supply of power to the vaporizer based on the electrical resistance of the vaporizer.

The electronic circuitry may comprise a controller with a microprocessor, which may be a programmable microprocessor. The electronic circuitry may comprise further electronic components. The electronic circuitry may be configured to regulate a supply of power to the vaporizer. Power may be supplied to the vaporizer continuously following activation of the system or may be supplied intermittently, such as on a puff-by-puff basis. The power may be supplied to the vaporizer in the form of pulses of electrical current.

The electronic circuitry may be configured to set or regulate a pumping frequency of the pump and/or to control the supply of power to the pump.

The aerosol-generating system may comprise a power supply (e.g., a battery) within the main body of the housing. The power supply may be a form of charge storage device such as a capacitor. The power supply may require recharging and may have a capacity that allows for the storage of enough energy for one or more periods of vapor or aerosol generation. For example, the power supply may have sufficient capacity to allow for the continuous generation of aerosol for a period of around six minutes or for a period that is a multiple of six minutes. In another example, the power supply may have sufficient capacity to allow for a desired or predetermined number of puffs or discrete activations of the heater assembly.

To allow ambient air to enter the aerosol-generating system, a wall of the housing of the aerosol-generating system may be provided with at least one semi-open inlet. The wall of the housing may be opposite to the vaporizer (e.g., a bottom wall). In a non-limiting embodiment, the semi-open inlet allows air to enter the aerosol-generating system while hindering or preventing air or liquid from leaving the aerosol-generating system through the semi-open inlet. A suitable semi-open inlet may, for example, be a semi-permeable membrane, which is permeable in one direction only for air, but is air- and liquid-tight in the opposite direction. A semi-open inlet may, for example, also be a one-way valve. The semi-open inlets may be configured to allow air to pass through the inlet only if specific conditions are met (e.g., when there is a depression in the aerosol-generating system or a volume of air passing through the valve or membrane that meets a threshold value). The aerosol-generating system may have an additional air inlet for ambient air to be sucked into by the operating pump.

The liquid aerosol-forming substrate is a substrate capable of releasing volatile compounds that can form an aerosol. The volatile compounds may be released by heating the liquid aerosol-forming substrate. The liquid aerosol-forming substrate may comprise a plant-based material. For example, the liquid aerosol-forming substrate may comprise tobacco. The liquid aerosol-forming substrate may comprise a tobacco-containing material containing volatile tobacco flavour compounds, which are released from the liquid aerosol-forming substrate upon heating. The liquid aerosol-forming substrate may alternatively comprise a non-tobacco-containing material. The liquid aerosol-forming substrate may comprise homogenised plant-based material. The liquid aerosol-forming substrate may comprise homogenised tobacco material. The liquid aerosol-forming substrate may comprise at least one aerosol-former. The liquid aerosol-forming substrate may comprise other additives and ingredients, such as flavourants.

The aerosol-generating system may be portable. For example, the aerosol-generating system may have a size comparable to a cigar or cigarette. The aerosol-generating system may have a total length between approximately 30 millimetres and approximately 150 millimetres. The aerosol-generating system may have an external diameter between approximately 5 millimetres and approximately 30 millimetres.

According to some example embodiments, there is provided a method for generating an aerosol. The method may comprise providing a liquid storage portion for storing a liquid aerosol-forming substrate; pumping air, by a pump, into the liquid storage portion to push out, by the air pumped into the liquid storage portion, a volume of the liquid aerosol-forming substrate from the liquid storage portion to a vaporizer; and volatilizing, by the vaporizer, at least a part of the volume of the liquid aerosol-forming substrate pushed out from the liquid storage portion.

The volume of the liquid aerosol-forming substrate, in a further step, may be pushed out (e.g., free of air bubbles) from the liquid storage portion to the vaporizer.

The pump may be a micropump and may be configured to pump a desired or predetermined volume of air per pump activation.

A desired or predetermined volume of the liquid aerosol-forming substrate may, in a further step, be pushed out from the liquid storage portion to the vaporizer by one pump activation.

It should be understood that features described in relation to one or more examples above may equally be applied to other examples herein.

Figure 1A:
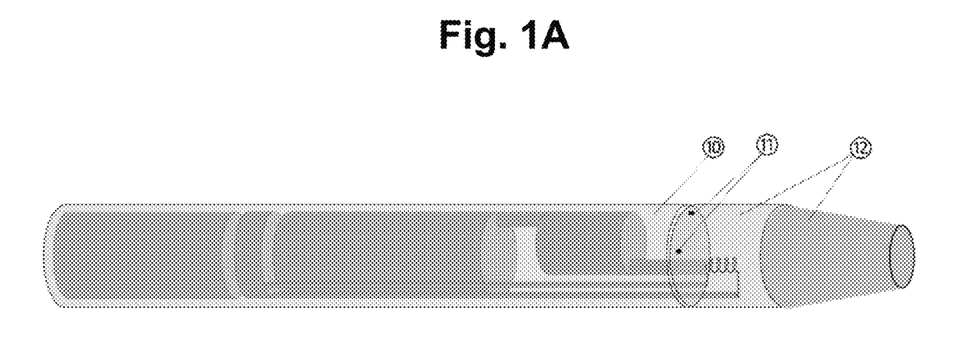
FIG. 1A and FIG. 1B are schematic views of an aerosol-generating system in accordance with an example embodiment.
Figure 1B:
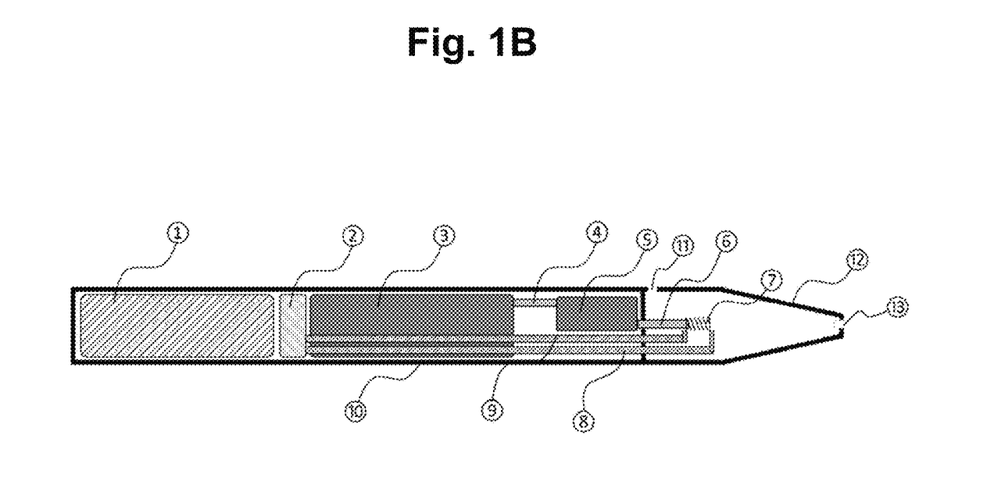

FIG. 1A and FIG. 1B show a schematic illustration of an aerosol-generating system of an example embodiment. The aerosol-generating system comprises a main unit and a refillable or exchangeable cartridge with a liquid storage portion 5. The liquid storage portion 5 is configured for storing a liquid aerosol-forming substrate. The main unit comprises a main body 10 and a mouthpiece portion 12. The main body 10 contains a power supply 1 (e.g., a battery such as a lithium iron phosphate battery), electronic circuitry 2, a cavity for holding a cartridge, a micropump 3, and a vaporizer 7. Electrical connectors 8, 9 are provided at the sides of the main body 10 to provide an electrical connection between the electronic circuitry 2, the power supply 1, and the vaporizer 7. The micropump 3 is configured, when being operated, to suck air into its inlet and to provide pumped air at its outlet. Tube 4 is provided to connect the outlet of the micropump 3 to the inlet of the liquid storage portion 5. When the micropump 3 operates, it pumps air via the tube 4, which is airtight to the environment, to the liquid storage portion 5. The compressed air pumped into the inlet of the liquid storage portion 5 pushes by displacement of a volume of liquid aerosol-forming substrate through the outlet of the liquid storage portion 5 into tube 6. Tube 6 leads the flow of liquid aerosol-forming substrate from the outlet of the liquid storage portion 5 to the deposition region of the heating element of the vaporizer 7. A rate of the flow of the liquid aerosol-forming substrate is determined by a pumping frequency of the micropump 3. The mouthpiece portion 12 comprises a plurality of air inlets 11 and an outlet 13. A negative pressure may be applied to the outlet 13 to draw air from the air inlets 11, through the mouthpiece portion 12, and to the outlet 13. Internal baffles may be provided to force the air flowing through the mouthpiece portion 12. The vaporizer 7 is configured to heat the liquid aerosol-forming substrate directly after the liquid aerosol-forming substrate exits the tube 6.

The cartridge is configured to be received in a cavity within the main body 10. The cartridge may be replaced when the aerosol-forming substrate provided in the cartridge is depleted. When inserting a new cartridge, a slider at the main body may be moved to expose the cavity. A new cartridge may be inserted into the exposed cavity. The inlet of the liquid storage portion 5 is configured to connect to the tube 4 connected to the outlet of the micropump 3. The outlet of the liquid storage portion 5 is configured to connect to the tube 6 connected to the vaporizer 7. In an example embodiment, the main unit is portable and has a size comparable to a cigar or cigarette.

Figure 2:
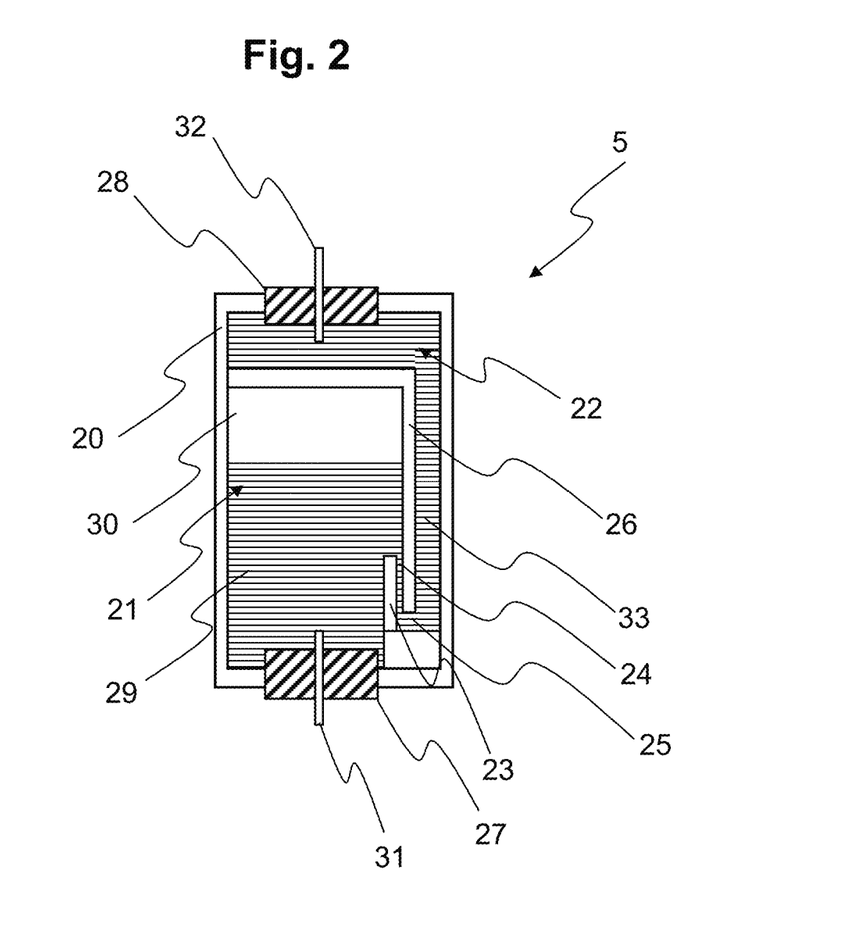
FIG. 2 is a cross-sectional view of a liquid storage portion of an aerosol-generating system in accordance with an example embodiment.

FIG. 2 is a cross-sectional view of a liquid storage portion of an aerosol-generating system in accordance with an example embodiment. The liquid storage portion 5 shown in FIG. 2 corresponds to the liquid storage portion 5 shown in FIG. 1B. The liquid storage portion 5 is configured as a tank or reservoir for storing a liquid aerosol-forming substrate 29. The liquid storage portion 5 comprises a housing 20, a first membrane 27 (e.g., first self-healing pierceable membrane) at the bottom of the housing 20, and a second membrane 28 (e.g., second self-healing pierceable membrane) at the top of the housing 20. The housing 20 and the membranes 27 and 28 define an inner volume of the liquid storage portion 5 that is hermetically sealed from the outer environment. The inner volume is divided by a separating unit into a first storage volume 21 and a second storage volume 22.

In an example embodiment, the separating unit is formed by a first dividing wall 23 and a second dividing wall 26. The first dividing wall 23 extends longitudinally in the direction from the bottom to the top of the liquid storage portion 5. The second dividing wall 26 almost fully separates the first storage volume 21 and the second storage volume 22 from each other except a gap 25 close to the bottom of the liquid storage portion 5. The first dividing wall 23 and the section of the second dividing wall 26 ending at the gap 25 are mounted facing each other at a distance for defining a vertical gap 24. The vertical gap 24 extends longitudinally in the direction from the bottom to the top of the liquid storage portion 5. The first storage volume 21 and the second storage volume 22 are separated by gap 25 and vertical gap 24 from each other. A one-way valve (not shown) allowing the liquid aerosol-forming substrate 29 to pass from the first storage volume 21 to the second storage volume 22 and blocking air from passing to the second storage volume 22 may be arranged in the vertical gap 24. The first storage volume 21 is configured for the storing the liquid aerosol-forming substrate 29 and a volume of air 30. A portion of the second dividing wall 26 extends longitudinally from the gap 25 in the direction from the bottom to the top of the liquid storage portion 5. The arrangement of the second dividing wall 26 establishes in the second storage volume 22 a dip tube 33 extending longitudinally in the direction from the bottom to the top of the liquid storage portion 5. The gaps 24, 25 and the dip tube 33 are arranged relative to each other such that air bubbles are inhibited from passing from the first storage volume 21 to the second storage volume 22 over a wide range of orientations of the liquid storage portion 5. Thus, only the liquid aerosol-forming substrate 29 (without any air bubbles) is stored in the second storage volume 22 over a wide range of orientations. This allows liquid dispensing that is air bubble free over a wide range of orientations of the liquid storage portion 5. The range of orientations may be between 0 and ±90 degrees for liquid dispensing that is air bubble free. FIG. 2 shows an orientation of approximately 0 degrees according to an example embodiment. In the orientation of the liquid storage portion 5 shown in FIG. 2, the outlet of the liquid storage portion 5 is located at the top, and the inlet is located at the bottom of the liquid storage portion 5 or at least below the fill level. In the desired usage orientation, the dividing wall(s) and the gap(s) ensure that no air 30 passes from the first storage volume 21 to the second storage volume 22. Air bubbles may be hindered or prevented from passing into the second storage volume 22 if the liquid storage portion 5 is not inclined more than 90 degrees compared to the upright position depicted in FIG. 2.

The liquid storage portion 5 shown in FIG. 2 may be coupled to the micropump 3 shown in FIG. 1B by piercing an end of tube 31, which may correspond to tube 4 of FIG. 1B, through the first self-healing pierceable membrane 27. Furthermore, the liquid storage portion 5 may be coupled to the vaporizer 7 shown in FIG. 1B by piercing an end of tube 32, which may correspond to tube 6 of FIG. 1B, through the second self-healing pierceable membrane 28. For dispensing a volume of liquid aerosol-forming substrate 29 stored in the second storage volume 22 through the tube 32 to the vaporizer 7, the micropump 3 pumps air through the tube 31 into the first storage volume 21. In response to the pumped air, a volume of liquid aerosol-forming substrate 29 stored in the first storage volume 21 is displaced through the gaps 24, 25 to the second storage volume 22, thus resulting in the dispensing the same volume of liquid aerosol-forming substrate 29 from the second storage volume 22 through the tube 32. The air pumped into the liquid storage portion 5 is collected in the first storage volume 21.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An aerosol-generating system, comprising:
    a cartridge containing an aerosol-forming substrate; and
    a main unit configured to pump an incoming volume of air
        into the cartridge to displace an outgoing volume of the aerosol-forming substrate from the cartridge and to heat the outgoing volume of the aerosol-forming substrate to generate an aerosol.

2. The aerosol-generating system of claim 1, wherein the cartridge defines an inlet for the incoming volume of the air and an outlet for the outgoing volume of the aerosol-forming substrate.

3. The aerosol-generating system of claim 2, wherein the inlet is the only point of ingress into the cartridge, and the outlet is the only point of egress from the cartridge.

4. The aerosol-generating system of claim 2, wherein the cartridge further defines a first storage volume and a second storage volume containing the aerosol-forming substrate.

5. The aerosol-generating system of claim 4, wherein the cartridge includes a first dividing wall and a second dividing wall configured to partition the first storage volume and the second storage volume.

6. The aerosol-generating system of claim 5, wherein the first dividing wall and the second dividing wall are configured inhibit a passage of the incoming volume of the air through the cartridge.

7. The aerosol-generating system of claim 5, wherein the first dividing wall and the second dividing wall have overlapping portions.

8. The aerosol-generating system of claim 7, wherein the overlapping portions of the first dividing wall and the second dividing wall define a gap therebetween.

9. The aerosol-generating system of claim 8, wherein the first storage volume is in fluidic communication with the second storage volume via only the gap.

10. The aerosol-generating system of claim 4, wherein the cartridge is configured such that the incoming volume of the air is confined to the first storage volume.

11. The aerosol-generating system of claim 4, wherein the main unit is configured to pump the incoming volume of the air into the first storage volume via the inlet in the cartridge.

12. The aerosol-generating system of claim 4, wherein the cartridge is configured such that the outgoing volume of the aerosol-forming substrate displaced therefrom is from the second storage volume.

13. The aerosol-generating system of claim 1, wherein the main unit defines a cavity configured to receive the cartridge.

14. The aerosol-generating system of claim 1, wherein the main unit includes a micropump upstream from the cartridge, the micropump configured to pump the incoming volume of the air into the cartridge.

15. The aerosol-generating system of claim 1, wherein the main unit includes a vaporizer downstream from the cartridge, the vaporizer configured to heat the outgoing volume of the aerosol-forming substrate.

* * * * *

UNITED STATES PATENT AND TRADEMARK OFFICE
CERTIFICATE OF CORRECTION

PATENT NO.         : 10,980,287 B2
APPLICATION NO.    : 16/875355
DATED              : April 20, 2021
INVENTOR(S)        : Ben Mazur et al.

It is certified that error appears in the above-identified patent and that said Letters Patent is hereby corrected as shown below:

On the Title Page

Item (71) Applicant: reads "Mycronic AB, Taby (SE)" should read --Altria Client Services LLC, Richmond, VA (US)--

Signed and Sealed this
Thirtieth Day of August, 2022

Katherine Kelly Vidal
*Director of the United States Patent and Trademark Office*